Figure 1:
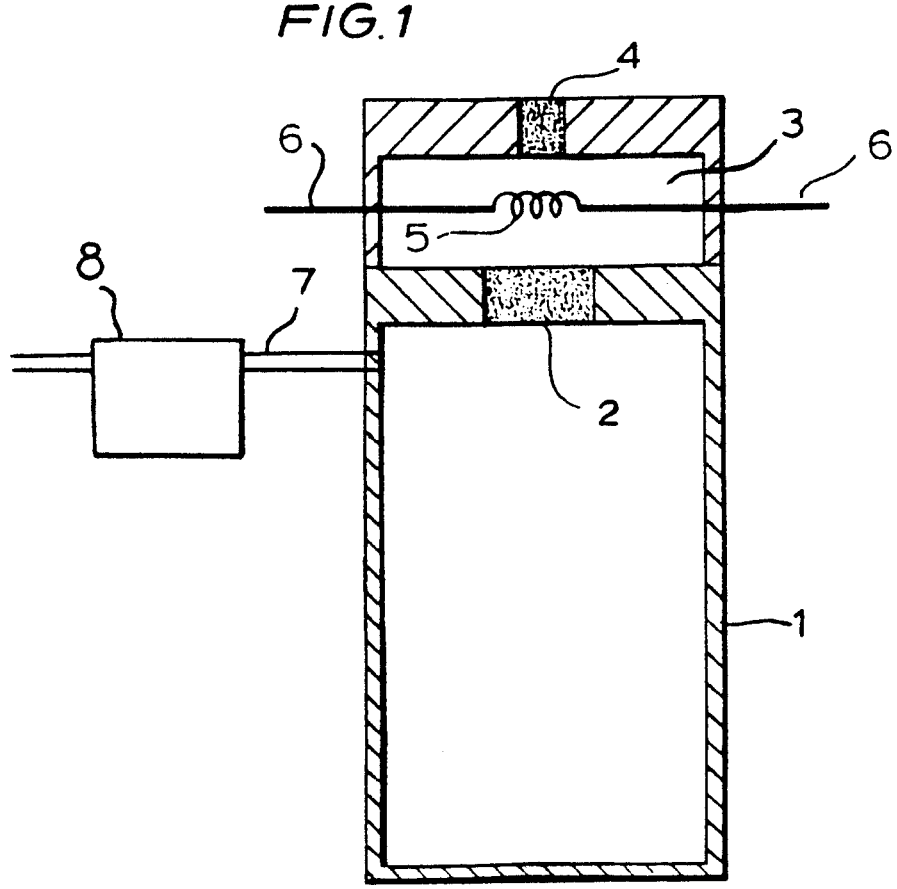

United States Patent [19]

Tantram

[11] Patent Number: 5,070,721
[45] Date of Patent: Dec. 10, 1991

[54] FLAMMABLE GAS DETECTION

[75] Inventor: Anthony D. S. Tantram, Great Bookham, England

[73] Assignee: City Technology Ltd., London, England

[21] Appl. No.: 617,596

[22] Filed: Nov. 26, 1990

[30] Foreign Application Priority Data

Dec. 13, 1989 [GB] United Kingdom ............... 89828177

[51] Int. Cl.$^5$ ........................................... G01N 27/16
[52] U.S. Cl. ..................................... 73/23.31; 422/94
[58] Field of Search ......................... 73/23.31; 422/94

[56] References Cited

U.S. PATENT DOCUMENTS 3,421,362  1/1969  Schaffer .......................... 422/94 X
3,607,084  9/1921  Mackey et al. ................. 73/21.31 X
4,128,458  12/1978  Obiaya .......................... 422/94 X
4,305,724  12/1981  Micko .......................... 422/94 X

FOREIGN PATENT DOCUMENTS 8701453  3/1987  World Int. Prop. O. ............ 422/94

Primary Examiner—Hezron E. Williams
Assistant Examiner—Joseph W. Roskos
Attorney, Agent, or Firm—Stevens, Davis, Miller & Mosher

[57] ABSTRACT

An oxygen sensor (1) with an inlet (2) connects with a small chamber (3). An inlet provided with a diffusion barrier (4) permits flammable gas and oxygen to enter the chamber. The oxygen concentration within the chamber is low, and a catalytic element (5) within the chamber causes combustion of flammable gas, thus consuming oxygen within the chamber. The signal from the oxygen sensor is processed to calculate a concentration for the flammable gas.

11 Claims, 2 Drawing Sheets

FLAMMABLE GAS DETECTION

This invention concerns flammable gas detection, and more especially it concerns devices and methods for detecting and measuring flammable gases or vapors.

Flammable gases and vapors constitute a wide spread explosion hazard in many industrial or domestic situations. Each such gas has critical values of concentration in air, namely a lower explosive limit, LEL, and an upper explosive limit, UEL. When the concentration of the gas is between these limits, any ignition source such as a spark, can trigger an explosion.

The well established and almost universally used method for the detection and measurement of flammable gases is based on the principle of measuring the increase in temperature of a heated filament, usually catalysed, resulting from the heat of combustion of the flammable gas thereon. The filament is usually a coil of thin platinum wire upon which is formed a bead of supported catalyst, and such a bead is commonly known as a pellistor. The filament is heated by an electric-current to the temperature necessary to ensure combustion of the flammable gas on the surface of the supported catalyst. This results in an increase of temperature, and a consequent increase in the resistance of the platinum coil. The active pellistor element is usually matched with a similar, but catalytically inactive, element, in the opposite arm of a Wheatstone bridge circuit in order to compensate for variations in ambient temperature, and the off-balance current forms the signal that is a measure of the concentration of flammable gas.

It will be seen that the platinum filament performs more than one function. It is not only the heating element, but also the measuring element, and for this reason has to be constructed with a high degree of precision.

The disadvantages of this method are (a) a high power consumption, because of the two elements to be heated, which has particular relevance to portable battery powered monitors, (b) susceptibility to catalyst poisons, and (c) a limited range which can lead to ambiguous readings. The range is limited by the stoichiometry of the combustion reaction. For example, with methane $$CH_4 + 2O_2 \rightarrow CO_2 + 2H_2O$$

it can readily be shown that at a methane concentration of 9.46% in air, all the oxygen will be consumed, and at higher concentrations the signal will be controlled by the oxygen rather than the methane. Furthermore, it can be seen that signals in very high methane concentrations can be identical to those in low methane concentrations, and so give rise to ambiguous readings. For example, the signal from 1% methane, balance air, will be approximately the same as that for 90.4% methane, balance air.

It is an object of the present invention to avoid or at least to reduce these disadvantages by employing a fundamentally different principle of measurement. The present invention provides a device for detecting and/or measuring flammable gas in the presence of oxygen, which device comprises an oxygen sensor having an inlet, a chamber having an inlet for gas to be sensed for the presence of flammable gas, said chamber inlet having a diffusion barrier which substantially controls the rate of diffusion of gas into said chamber, the sensor inlet having a relatively low diffusion resistance to oxygen compared to the diffusion resistance of the diffusion barrier, and said chamber containing means to ensure combustion of flammable gas therein.

The invention further provides a method of detecting and/or measuring flammable gas in the presence of oxygen, which method comprises admitting a gas into a chamber through a diffusion barrier, combusting flammable gas within the chamber, sensing the oxygen content within the chamber using an oxygen sensor which produces a signal indicative of oxygen content within said chamber, the diffusion resistance of the inlet to the oxygen sensor being relatively low in comparison to the diffusion resistance of the diffusion barrier, whereby the concentration of oxygen within the chamber is maintained below that of the gas outside the chamber, and processing the signal from the oxygen sensor to calculate a value for the concentration of the flammable gas.

In the following description of the invention, methane will be used as an example of an inflammable gas, but it will readily be appreciated that the invention is applicable to any flammable gas.

The means to ensure combustion is suitable an electrically heated element such as a filament with a catalytic coating, a pellistor, any other effective resistance heating element, or means such as an electric discharge. It has been found, however, that a simple heated platinum filament is quite satisfactory in tests utilizing methane as the flammable gas. The term "filament" will be used herein to include ribbons, coils and all suitable heating means including thick films. The necessary temperature at which the filament should be run to ensure complete combustion may be found by routine experiments. It is preferable to maintain a constant supply voltage once the voltage to achieve the desired temperature has been established; there are methods well known in the art for providing constant voltage. It will be seen that since the filament does not form part of the measuring system, a less expensive construction and/or less precision is required. Power consumption can also be significantly reduced as compared to the paired pellistors of the prior art, simply because paired filaments are not required.

The diffusion barrier may take the form of a non-porous plastic membrane. Preferably, it is a gas phase diffusion barrier as described in UK Patent Specification GB 1 571 282, comprising a porous body or a capillary, or a combination of the two. Another suitable barrier is a Knudsen diffusion barrier as described in UK Patent Specification GB 2 049 952, or may be any combination of the above. For applications where flame proofing is necessary a suitable metal sinter disc or piece may be used to form the whole or part of the diffusion barrier. The extent of restriction of flow of gas is described below.

The oxygen sensor is suitable of the galvanic oxygen-consuming type. A potentiometric galvanic oxygen-consuming sensor is especially preferred. It may be a solid state sensor, e.g. a zirconia-based electrolyte oxygen sensor, but this has the disadvantage that it requires additional power to heat it to an operating temperature, and accordingly it is preferred to use a low temperature oxygen sensor. Electrochemical sensor cells, including solid electrolyte cells, are particularly preferred. The oxygen sensor characteristics should desirably be chosen in conjunction with the characteristics of the diffusion barrier, so that the diffusion barrier provides the controlling restriction to diffusion into the total device. This can be achieved by measuring (a) the sensitivity of the oxygen sensor itself, i.e. current per unit concentration of oxygen, and (b) the sensitivity of the total device to oxygen with the combustion means inactive. Sensitivity (a) should be at least two times sensitivity (b), and is preferably at least five times, more preferably at least a factor of 10, and in general, the higher the better.

The chamber is suitably moulded, cast or machined, e.g. in a disc incorporating the diffusion barrier in an inlet bore. The material of the walls of the chamber is preferably resistant to heat, and may be metal or ceramic. The chamber should have as small a volume as possible to achieve the best response time. Although the volume may vary according to the other components of the device, it is preferably less than 2 ml, more preferably within the range 0.01 to 0.5 ml. If the device is operated with the combustion means inactive, the device will act as an oxygen sensor whose sensitivity is substantially controlled by the diffusion barrier, and the output signal will reflect the reduction in oxygen concentration resulting from the dilution effect of the methane, i.e. the signal will be $(1-0.01C)S^0$, where $S^0$ is the signal in pure air, e.g. 20.9% oxygen, and C is the concentration of methane in vol. %.

When the combustion means is operating, methane entering the chamber will be oxidised according to the above equation, so that 1 mol of methane will remove 2 mols of oxygen, and the rate of removal of oxygen by this reaction will subtract from the otherwise expected oxygen signal. This change in signal will be a function of the stoichiometry of the combustion reaction and of the relative diffusion rates of methane and oxygen through the diffusion barrier, which will be a function of the methane concentration and hence give a measure of the methane concentration.

For example, if the diffusion coefficient of methane through the diffusion barrier is 1.41 times that of oxygen, it can be shown that the resulting net signal will be $$S^0(1-0.145C)$$

The consequence of this is that the sensor signal relative to the signal in 100% pure air drops to zero at 6.9% methane, and remains at zero for all higher methane concentrations. Although the range of the device is thus limited to this value of 6.9% methane, the problem of ambiguous signals is no longer present. A similar effect, but with different maximum ranges, is observed for other flammable gases such as the higher hydrocarbon gases and hydrogen. If the device uses the preferred Knudsen diffusion barrier or gas phase barrier mentioned above, the diffusion rates are inversely proportional to the square root of the gas molecular weight, at least to a first approximation.

The invention will now be described by way of example only, by reference to

FIG. 1 of the accompanying drawings, which is a schematic cross-section of a device according to the invention.

Figure 2:
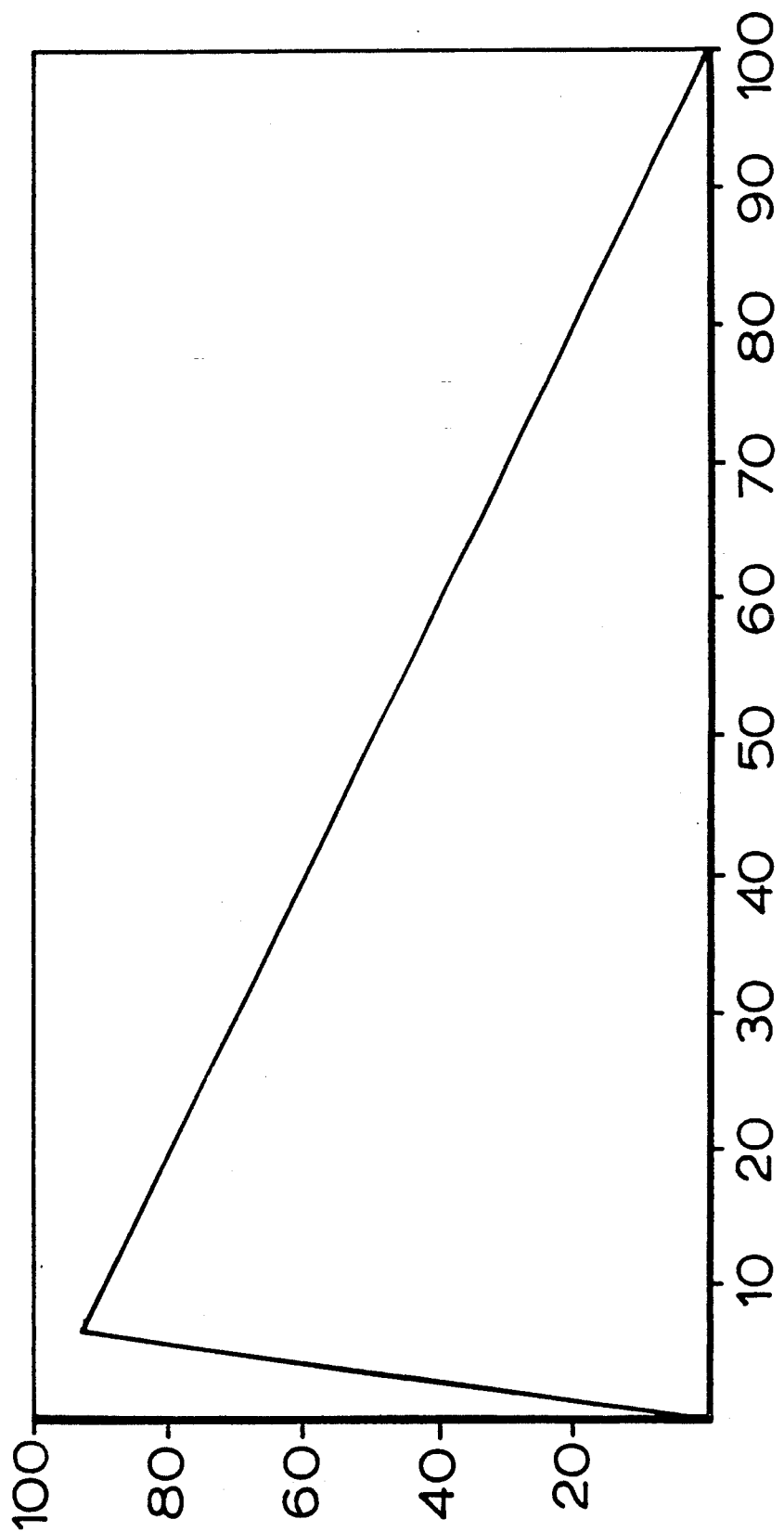

FIG. 2 is a plot of the signal from an embodiment of the invention, against concentration of methane.

Referring to FIG. 1, the device comprises an oxygen sensor, 1, which is suitably a galvanic oxygen-consuming oxygen sensor marketed by City Technology Ltd of London under the Registered Trade Mark "CiTiceL", and which sensor has an inlet, 2. Sealed onto the sensor is a chamber, 3, which has an inlet, 4, which comprises or acts as a diffusion barrier, the diffusion resistance of this barrier being relatively high for oxygen compared to the diffusion resistance of the sensor inlet, 2. Sealed into the chamber 3, is a thin platinum wire coil, 5, having leads, 6, extending outside the chamber for connection to a direct current source to enable it to be heated to a combustion temperature. The oxygen sensor has output leads 7 for connection to suitable signal processing means 8, which may include analogue or digital circuitry, such as a suitably programmed or dedicated microprocessor or microcomputer. The microprocessor or microcomputer may use conventional technology such as look-up tables to establish a methane concentration value, which can be signalled to a display. The skilled man may readily develop alternative signal processing. The diffusion barrier substantially controls the flux of oxygen, and the concentration of oxygen in the chamber is low.

The device of the invention offers advantages in comparison to pellistors in that it is very much more resistant to poisoning. A standard pellistor is required to show a resistance to $H_2S$ at a concentration of 100 ppm in a gas mixture containing 2.5% methane in air plus additional nitrogen resulting from blending (e.g. blending 1000 ppm $H_2S$ in $N_2$ with 2.5% $CH_4$ in air to give the desired $H_2S$ concentration), such that the pellistor takes 2 minutes or more to show a 20% drop in output. A so-called "poison-resistant" pellistor stabilises its output at about a 10% drop after 5 minutes exposure. Tests carried out with a prototype device according to the invention showed no loss in output after 180 minutes exposure to the test gas. The device was then exposed to 500 ppm $H_2S$ for 100 minutes, and again showed no discernable loss in output.

Tests indicate that power consumptions of approximately 310 mA at 1.1 V to 320 mA at 1.2 V are suitable to ensure complete combustion of methane using a platinum filament. A chamber volume of 0.03 cc was used in the test, being a groove 2 mm $\times$ 2.5 mm $\times$ 6 mm machined in a disc, and having a Pt coil positioned therein. A 1 mm diameter bore connects the chamber to the outside atmosphere and acts as the inlet to the chamber. The disc is fitted to seal onto the inlet of a commercial oxygen sensor, the inlet having an appreciably lower diffusion resistance than the chamber inlet.

The operation of the device is as described above, but the measuring range is limited, and the signal would be affected by the presence of an inert gas which would not be an explosion hazard, although it could form a hypoxia hazard.

The above mentioned difficulties may be overcome by the use of two further embodiments of the invention.

In a further embodiment, the device of the invention described with reference to FIG. 1, is used in combination with a second galvanic oxygen sensor, of the same type but not using any chamber. The second oxygen sensor is used to produce a signal which is used to back off the signal from the device, and is set up so that in pure air, the net signal is zero. The response of this embodiment is illustrated by accompanying FIG. 2, which is a plot for methane where the x-axis represents % methane by vol, and the y-axis represents the net signal as a % of the signal of the oxygen sensor in pure air. It can be seen that the combination embodiment can be used to measure the full concentration range. The combined net signal still suffers from the ambiguity problem, but this can be eliminated by suitable processing of the signal, e.g. with a microprocessor, since one can still monitor the signals from the device and from the oxygen sensor. At the low end of the concentration range, the net signal may be used, but as soon as the signal from the device with its combustion means drops to zero, the signal from the second sensor is used as the measure of concentration. At low concentrations, when the net signal is being used, any effect of inert gas is cancelled out, although it will affect signals in the higher range where the second signal alone is being used. The combination also provides a combined flammable gas and oxygen sensor, since the signal from the second sensor gives a direct measurement of oxygen concentration.

In another embodiment, the device as described in FIG. 1 is used in intermittent mode, i.e. with the combustion means alternatively switched on and off. With the element off, in the presence of methane for example, methane will diffuse into the chamber to reach a concentration similar to that outside, but the oxygen concentration in the chamber will be low. When the element is switched on, the methane in the chamber combusts, and the oxygen concentration falls to zero at a much lower methane concentration than was the case with the element on continuously. The effect is such that an enhanced signal is obtained, so enabling much lower concentrations of flammable gas to be measured. The signal from the device peaks and then, if the element is left on, decays to the steady state value. Using suitable peak detection and measurement circuitry, readily designed by a skilled electronics engineer, the peak signal can be used as the measure of flammable gas concentration with the benefit of increased sensitivity. The sensitivity will be higher, the more sensitive the oxygen sensor without the diffusion barrier is to oxygen, relative to the sensitivity of the device to oxygen with the diffusion barrier in place. When this embodiment is used in the intermittent mode, the signal with the combustion element off also provides a measure of oxygen concentration, so that the device may act as a combined oxygen sensor and flammable gas detector.

The device according to the invention is used in other aspects of the invention in combination with signal processing means, and with display and/or alarm means, which may be a visual and/or audible warning. The device is especially suitable to be incorporated into a hand-held or portable instrument which has utility in many industrial, domestic, mining etc situations.

I claim:

1. A device for sensing flammable gas in the presence of oxygen, which device comprises an oxygen sensor having an inlet, said sensor inlet being connected to a chamber having an inlet for gas to be sensed for the presence of flammable gas, said chamber inlet having a diffusion barrier which substantially controls the rate of diffusion of gas into said chamber, the sensor inlet having a relatively low diffusion resistance to oxygen compared to the diffusion resistance of the diffusion barrier, and said chamber containing means to ensure combustion of flammable gas therein.

2. A device as claimed in claim 1, wherein the means to ensure combustion is an electrically-heatable catalytic element.

3. A device as claimed in claim 1, wherein the volume of the chamber is less than 2 ml.

4. A device as claimed in claim 1, wherein the diffusion barrier is or comprises a Knudsen diffusion barrier, a capillary or a porous body.

5. A device as claimed in claim 1, wherein the sensitivity of the oxygen sensor is at least five times the sensitivity of the whole device to oxygen with the combustion means inactive.

6. A device as claimed in claim 1, comprising also signal processing means to calculate a concentration of flammable gas.

7. A device as claimed in claim 1, wherein the oxygen sensor is a galvanic oxygen-consuming sensor.

8. A method of sensing flammable gas in the presence of oxygen, which method comprises admitting a gas into a chamber through a diffusion barrier, combusting flammable gas within the chamber, sensing the oxygen content within the chamber using an oxygen sensor which produces a signal indicative of oxygen content within said chamber, the diffusion resistance of the inlet to the oxygen sensor being relatively low in comparison to the diffusion resistance of the diffusion barrier whereby the concentration of oxygen within the chamber is maintained below that of the gas outside the chamber, and processing a signal from the oxygen sensor to calculate a value for the concentration of the flammable gas.

9. A method as claimed in claim 8, wherein an electrically heated catalytic element is used to ensure combustion of flammable gas within the chamber.

10. A method as claimed in claim 8, wherein a further oxygen sensor without a chamber is used to back off the signal from said oxygen sensor, whereby a net signal is obtained covering the full range of flammable gas concentrations, and the net signal and/or the signal from the further oxygen sensor is processed to obtain a value for the concentration of flammable gas.

11. A method as claimed in claim 8, wherein the combustion of flammable gas is intermittently caused, and the fluctuations in signal from the oxygen sensor are measured and processed to indicate a concentration of flammable gas.

* * * * *